United States Patent [19]
Parks et al.

[11] Patent Number: 5,506,415
[45] Date of Patent: Apr. 9, 1996

[54] METHOD AND APPARATUS FOR COUNTING PHOTONS IN A SINGLE-MODE, COHERENT MICROWAVE FIELD

[76] Inventors: Allen D. Parks, 7309 Lord Barton Ct.; Kerry L. Beaver, 612 Greenbrier Ct., Apt. B, both of Fredericksburg, Va. 22401

[21] Appl. No.: 360,105

[22] Filed: Dec. 20, 1994

[51] Int. Cl.$^6$ .................................................. G01N 22/00
[52] U.S. Cl. .................. 250/336.1; 250/250; 250/338.1; 250/395
[58] Field of Search .............................. 250/336.1, 395, 250/338.1, 340, 250

[56] References Cited

U.S. PATENT DOCUMENTS 4,024,396  5/1977  Hill et al. ............................ 250/338.1

*Primary Examiner*—Carolyn E. Fields
*Assistant Examiner*—Edward J. Glick

[57] ABSTRACT

A method and apparatus are provided for determining the number of photons in a single-mode, coherent microwave field. A plurality of Rydberg atoms are generated whereby each Rydberg atom has an energy state defined by a plurality of energy levels. The Rydberg atoms are passed through the microwave field one at a time. An exit state of the microwave field in terms of phase is measured as each Rydberg atom exits the microwave field. An exit energy level of each Rydberg atom exiting the microwave field is also detected. The number of Rydberg atoms exiting the microwave field in each of four measurement classes defined by the exit state and exit energy level are counted.

12 Claims, 2 Drawing Sheets

METHOD AND APPARATUS FOR COUNTING PHOTONS IN A SINGLE-MODE, COHERENT MICROWAVE FIELD

The invention described herein relates generally to energy detection, and more particularly to a method and apparatus for counting photons in a single-mode, coherent microwave field.

BACKGROUND OF THE INVENTION

Current approaches to counting photons in a microwave field are either incapable of measuring small numbers of photons or disrupt the microwave field by either total destruction thereof during the measurement process or decimation of its photon distribution.

Accordingly, it is an object of the present invention to provide a method and apparatus for counting photons in a microwave field without destroying the microwave field or disrupting the underlying photon distribution in the microwave field.

Another object of the present invention is to provide a method and apparatus for counting photons in a dilute, single-mode coherent microwave field.

SUMMARY OF THE INVENTION

In accordance with the present invention, a method and apparatus are provided for counting photons in a single-mode, coherent microwave field. Toward that end, a plurality of Rydberg atoms are generated whereby each Rydberg atom has an energy state defined by a plurality of energy levels that includes a linear superposition of first and second of such energy levels. The first energy level serves as a reference for the microwave field while the second energy level possesses different energy and parity than the first energy level. The Rydberg atoms are passed through the microwave field one at a time. An exit state of the microwave field in terms of phase is measured as each Rydberg atom exits the microwave field. The exit state defines one of an unchanged phase in the microwave field or a finite phase shift in the microwave field. The energy level of each Rydberg atom exiting the microwave field is also detected. The exit energy level upon measurement is equal to either the first energy level or the second energy level. As a result, four measurement classes are defined as a function of the exit state and the exit energy level. The first measurement class correspond to the exit state of unchanged phase and the exit energy level equal to the first energy level. The second measurement class corresponds to the exit state of unchanged phase and the exit energy level equal to the second energy level. The third class corresponds to the exit state of finite phase shift and the exit energy level equal to the first energy level. The fourth measurement class corresponds to the exit state of finite phase shift and the exit energy level equal to the second energy level. The number of Rydberg atoms exiting the microwave field in each of the four measurement classes are counted. These counts are used to determine the number of photons in the microwave field.

BRIEF DESCRIPTION OF THE DRAWINGS

Other objects, advantages and novel features of the invention will become apparent from the following detailed description when considered in conjunction with the accompanying drawing, wherein.

DETAILED DESCRIPTION OF PREFERRED EMBODIMENT

Figure 1:
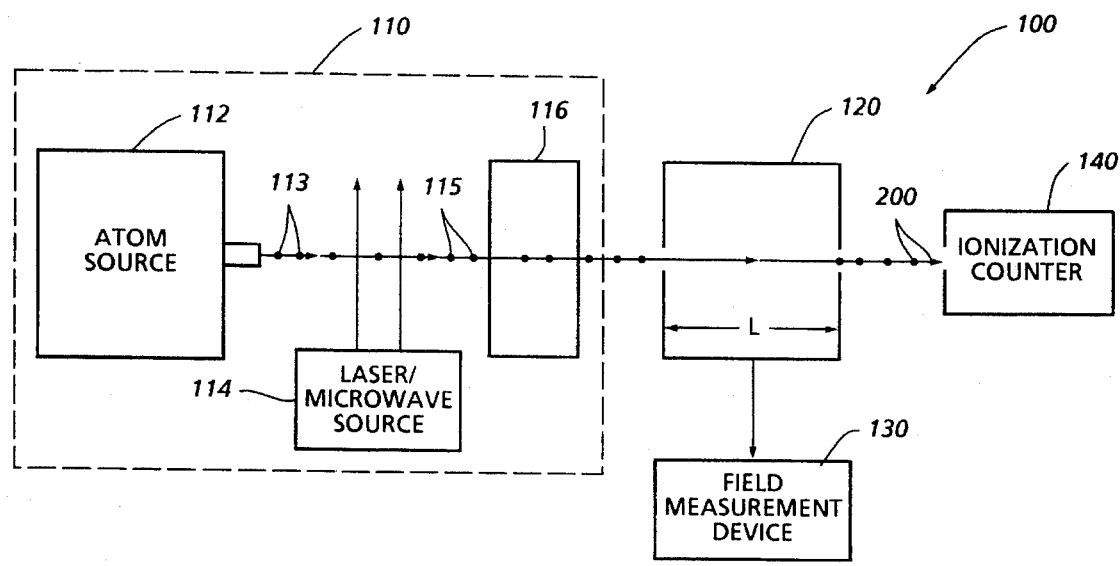
FIG. 1 is a schematic diagram of the apparatus used to carry out the method of the present invention.

Referring now to the drawing in detail, the method of the present invention according to one embodiment is performed by apparatus 100 as depicted in FIG. 1, wherein a single-mode microwave field is stored in a non-absorbing, microwave field storage container 120 in accordance with the well known Planck energy relationship:

$$\Delta E = \frac{h\omega}{2\pi}, \tag{1}$$

where $\Delta E$ is the energy of a field photon, h is Planck's constant, and $\omega$ is the field photon frequency. The microwave field stored in container 120 contains some number N of photons determined by the present invention.

Figure 2:
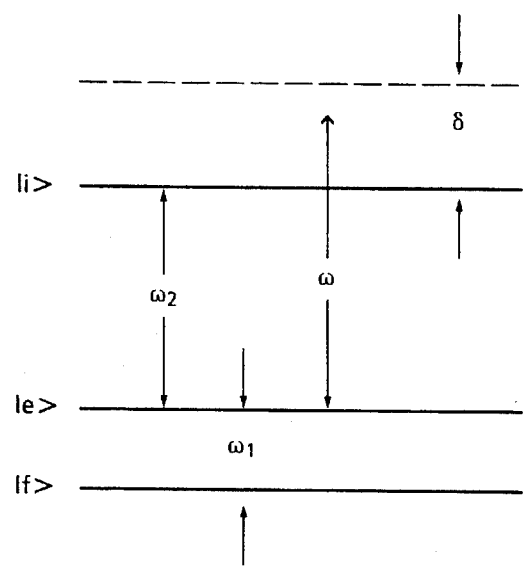
FIG. 2 is an energy level configuration diagram depicting the relationship between the Rydberg probe atoms and the microwave field of interest according to the preferred embodiment of the present invention.

As diagrammed in FIG. 1, an atomic probe species generator 110 generates a succession of probe atoms 200, each of which possesses a highly excited Rydberg state configuration defined by states $|f\rangle$, $|e\rangle$ and $|i\rangle$ as depicted in FIG. 2. States $|i\rangle$ and $|f\rangle$ must have the same parity and be opposite to that of $|e\rangle$. The energy corresponding to state $|e\rangle$ serves as a reference energy level, e.g., a lowest energy level, associated with the microwave field stored in container 120. The energy under state $|f\rangle$ must be different, i.e., greater or less than, the energy under state $|e\rangle$. The difference in energy between states $|e\rangle$ and $|f\rangle$ defines frequency $\omega_1$. The energy associated with state $|i\rangle$ is greater than that of state $|e\rangle$. In addition, state $|i\rangle$ must be detuned from the microwave field stored within container 120 such that frequency $\omega_2$ (representing the energy difference between states $|e\rangle$ and $|i\rangle$) is less than frequency $\omega$ by an amount $\delta$. The selection of $\delta$ should satisfy the relationship $(\Omega/\delta)^2 N \ll 1$ for container 120, where N is the number of photons and $\Omega$ is the vacuum Rabi coupling which is dependent upon the probe atom's position within container 120. To generate probe atoms 200, atomic species generator 110 as diagrammed in FIG. 1 includes atom source 112 (e.g., an oven and beam collimator) for generating a succession of atoms 113 whose energy state is lower than that of the reference state $|e\rangle$ for the microwave field stored within container 120. The generation of atoms 113 can be accomplished in a variety of ways well known in the art. For example, alkali atoms (e.g., lithium, sodium, etc.) maintained in an oven (not shown) could provide an atomic vapor of atoms that can then be formed into a beam by traditional beam collimator techniques (e.g., ionize the atoms; direct and accelerate the atoms with magnetic fields to form a beam having the proper atomic speed and needed separation between successive atoms; and reattach the electron or "un-ionize" the atoms).

Atoms 113 are next excited by lasers and microwave transfers from laser/microwave source 114 into state $|e\rangle$ as represented by atoms 115. Atoms 115 are then passed through region 116, e.g., a Ramsey zone, containing an auxiliary microwave field of frequency $\omega_1$. As a result, probe atoms 200 leave region 116 of the generator 110 in a state that is a linear superposition of states |e⟩ and |f⟩. The linear superposition of states |e⟩ and |f⟩ is given by $$|\Psi_p\rangle = \cos\left[\frac{\Omega'\tau}{2}\left(\frac{v_0}{v}\right)\right]|e\rangle - \sin\left[\frac{\Omega'\tau}{2}\left(\frac{v_0}{v}\right)\right]|f\rangle, \quad (2)$$

where $\Omega'$ is the Rabi coupling for region 116, $\tau$ is the transit time for one of atoms 115 to traverse region 116 at reference speed $v_0$, and $v_0/v$ is a ratio of reference speed-to-actual speed of the atom traversing region 116.

Probe atoms 200 are so spaced as to traverse container 120 sequentially, one at a time. Once in container 120, there is a coupling between the microwave field in container 120 and the atomic dipole of the |e⟩→|i⟩ transition which can produce a field phase shift. The presence of state |i⟩ allows each of probe atoms 200 to interact with the microwave field stored in the cavity of container 120 such that each of probe atoms 200 emerges therefrom in a correlated state given by:

$$|\phi\rangle = e^{-i\omega_1't_0}\beta|\Psi^l(t_0)\rangle|e\rangle + \gamma|\Psi^{l-1}_f(t_0)\rangle|f\rangle, \quad (3)$$

where $t_0$ is the time at which one of probe atoms 200 enters container 120,
$l(>1)$ is the number of probe atoms 200 that have traversed the container cavity, $$\beta = \cos\left[\frac{\Omega'\tau}{2}\left(\frac{v_0}{v}\right)\right], \quad (4)$$

$$\gamma = -\sin\left[\frac{\Omega'\tau}{2}\left(\frac{v_0}{v}\right)\right], \quad (5)$$

and $|\Psi^k_f(t_0)\rangle$ is the coherent field state evaluated at $t_0$ and is given by:

$$|\Psi^k_f(t_0)\rangle = e^{\frac{-i\omega t_0}{2}}\left|\alpha_0 e^{-i[\omega t_0 + k(\frac{v_0}{v})\epsilon]}\right\rangle. \quad (6)$$

In the foregoing equation $\alpha_0$ is a (possibly complex) constant not used in the method and $\epsilon$ is the accumulated probe atom phase shift per photon in container 120 for state |e⟩ given by:

$$\epsilon = \frac{\Omega_0^2}{2\delta}\left(\frac{L}{v_0}\right), \quad (7)$$

where $\Omega_0$ is the Rabi coupling at the center of container 120 and $L$ is the probe atom transit length for container 120.

When each of probe atoms 200 exits container 120, but before the next of probe atoms 200 enters container 120, the phase of the microwave field in container 120 is measured by field measurement device 130 which can be any one of a variety of devices well known in the art for non-destructively detecting phase shift in a microwave field. The phase shift, if present, is a result of the most recently passed through one of probe atoms 200. Thus, the outcome recorded by field measurement device 130 can be one of no phase shift or some finite amount of phase shift. The field measurement is relative to the phase of the microwave field just prior to the passing through of the most recent one of probe atoms 200. In addition to the field measurement, each of probe atoms 200 exiting container 120 is passed through ionization counter 140 where the state of the exiting probe atom in terms of its energy level is determined as being either one of |e⟩ or |f⟩. Thus the following field-probe measurement categories are created:

| Category Number | Field State    | Probe State |
|-----------------|----------------|-------------|
| I               | No phase shift | |e⟩         |
| II              | No phase shift | |f⟩         |
| III             | Phase shift    | |e⟩         |
| IV              | Phase shift    | |f⟩         |

The numbers of probes in each category are tallied and are used to calculate the number of photons N in container 120 where $$N = \frac{l_n X}{\left(\cos\left[\left(\frac{v_0}{v}\right)\epsilon\right] - 1\right)} \quad (8)$$

and $$X = \quad (9)$$

$$\frac{1}{4}\cot\left[\frac{\Omega'\tau}{2}\left(\frac{v_0}{v}\right)\right]\left[\left(\frac{1-a}{a}\right)^{1/2} + \left(\frac{1-b}{b}\right)^{-1/2}\right] +$$

$$\frac{1}{4}\tan\left[\frac{\Omega'\tau}{2}\left(\frac{v_0}{v}\right)\right]\left[\left(\frac{1-c}{c}\right)^{1/2} + \left(\frac{1-d}{d}\right)^{-1/2}\right]$$

Here $$a = \frac{J}{K+J},$$

$$b = \frac{K}{K+J},$$

$$c = \frac{P}{M+P},$$

and $$d = \frac{M}{M+P},$$

where
J = the number of category III probes;
K = the number of category IV probes;
M = the number of category I probes; and
P = the number of category II probes.

The parameters appearing in the foregoing equations can be tuned for various photon number regimes of interest. For example, using $\Omega'\tau = \pi/2$ and a monoenergetic beam output from atom source 112 of 10,000 atoms, the following values of $\epsilon$ provide average measurement errors of less than 2%.

| Photon Regime | $\epsilon$ |
|---------------|------------|
| [0,2)         | 1.500π     |
| [2,7)         | 1.800π     |
| [7,25)        | 1.900π     |
| [25,50)       | 1.950π     |
| [50,175)      | 1.970π     |
| [175,375)     | 1.980π     |
| [375,1000)    | 1.985π     |
| ≥1000         | 1.990π     |

The photon regime refers to a range of the number of photons expected to reside in the microwave field. For example, if the photon regime is expected to be between 25–50 photons, $\epsilon = 1.950\pi$ and reference speed $v_0$ is selected to yield this value of $\epsilon$. The more probes used in the process, the more accurate the measurement. Further, best results are generally obtained using a monoenergetic probe beam as the atom source 112. However, standard deviations up to 1% in $v_0/v$ still provide measurements with good average accuracies for the low photon number regime, e.g. <5% average error for the above parameter set and the [0, 125) regime.

Figure 3:
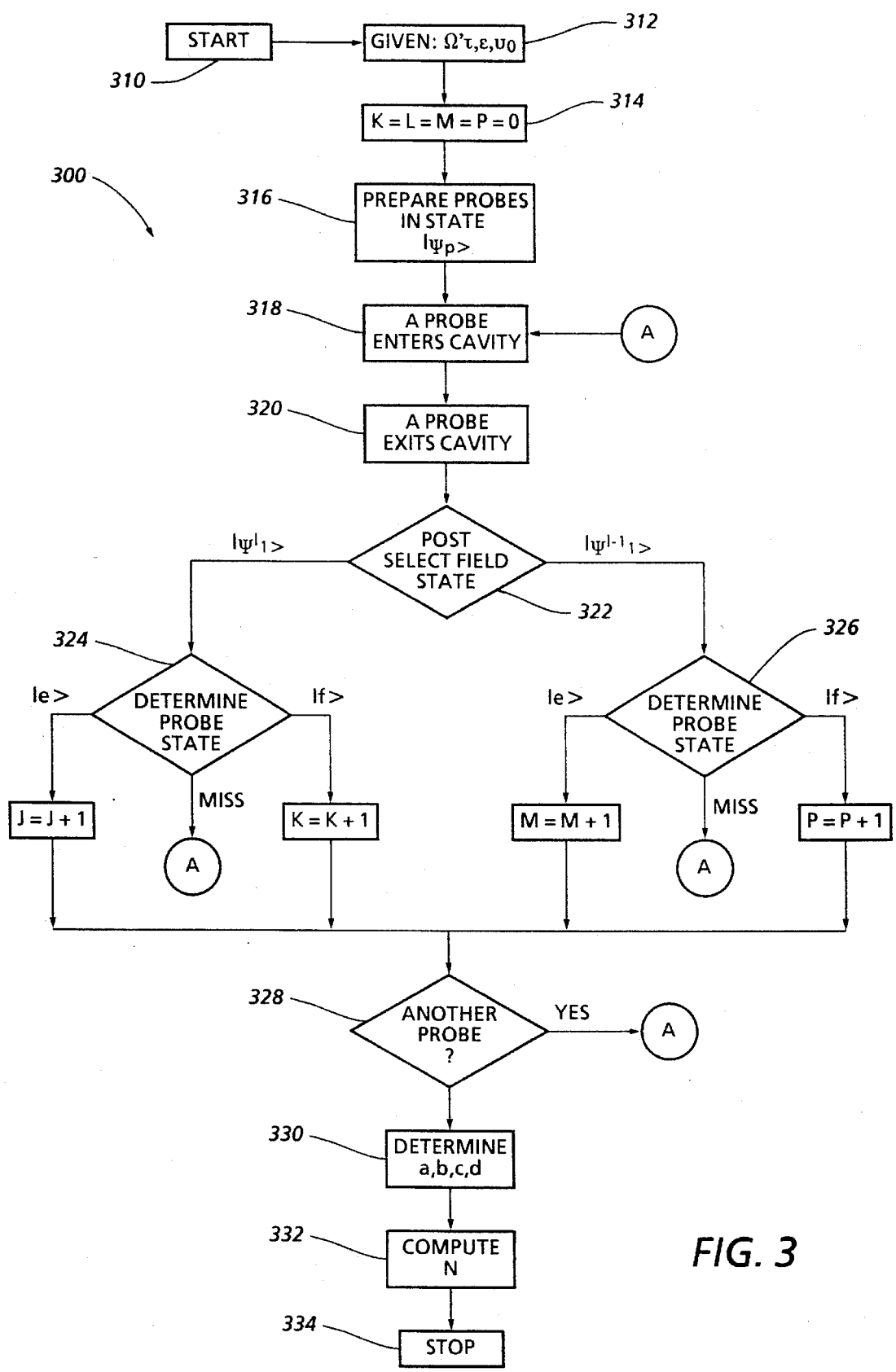
FIG. 3 is a block diagram illustrating the operational program associated with the apparatus diagrammed in FIG. 1.

The apparatus as hereinbefore described with respect to FIG. 1, is utilized to determine the number (N) of photons in the single-mode coherent microwave field within container 120 by means of an operational program 300 as diagrammed in FIG. 3. Such program is initiated, as denoted by step 310, by monitoring of activity within microwave region 116, as denoted by step 312. The monitored activity measurement data includes Rabi coupling ($\Omega'$), atom transient time ($\tau$) at a reference speed ($v_0$) and the accumulated probe atom phase per photon ($\epsilon$) under field state (|e>) within container 120. When the aforementioned number of field measurement category probes J, K, M and P reflected by the data measured by device 130 according to step 312 are equal to zero, as indicated by step 314, probe atoms in a linear superposition state (|$\Psi$p>) are prepared, as denoted by step 316. Such probe atoms 200 enter the microwave cavity of container 120, as denoted by step 318, followed by exit of the probe atoms from the microwave cavity as denoted by step 320. The probe atoms then enter the ionization counter 140 within which a count operation is programmed to determine the number (N) of the photons in the microwave field within container 120 as further diagrammed in FIG. 3.

Upon exit of the probe atoms from the microwave field in container 120, the counter operation is initiated by a post selection of the field state measured by device 130, as denoted by step 322 in FIG. 3. If the field state is determined to be phase shifted, then the probe state is measured to be either |e> or |f>, as denoted by step 324, and the appropriate probe category count J or K is increased by one and another probe is initiated as denoted by step 328. Another probe is also initiated if it is determined according to step 326 that the field is not phase shifted and the probe state is either |e> or |f>, producing a unit increase in probe category counts in M or P, respectively. When such probe categories J, K, M and P are suitable, according to step 328, calculations are performed to determine the aforementioned values of a, b, c and d as denoted by step 330, from which the photon number (N) is computed as indicated by step 332. The counting operational program as diagrammed in FIG. 3 is then completed as indicated by step 334.

The advantages of the present invention are numerous. Photon counts in a microwave field can be determined without destroying the field or decimating photon distribution. The method and apparatus are especially useful in the determination of photons in a dilute field because of the levels of sensitivity to small numbers of photons that can be achieved. The present invention will find utility in a wide variety of applications ranging from manufacturing processes to medical procedures. Thus, although the invention has been described relative to a specific embodiment thereof, there are numerous variations and modifications that will be readily apparent to those skilled in the art in the light of the above teachings. It is therefore to be understood that, within the scope of the appended claims, the invention may be practiced other than as specifically described.

What is claimed as new and desired to be secured by Letters Patent of the United States is:

1. A method of counting photons in a single-mode, coherent microwave field, comprising the steps of:

generating a plurality of Rydberg atoms, each of said plurality of Rydberg atoms having an energy state defined by a plurality of energy levels that includes a linear superposition of first and second energy levels, said first energy level serving as a reference energy level of said microwave field and said second energy level being of different energy and parity than said first energy level;

passing said plurality of Rydberg atoms through said microwave field one at a time;

measuring an exit state of said microwave field in terms of phase as each of said plurality of Rydberg atoms exits said microwave field, said exit state defining one of an unchanged phase in said microwave field or a finite phase shift in said microwave field;

detecting an exit energy level of each of said plurality of Rydberg atoms exiting said microwave field, said exit energy level being one of said first energy level and said second energy level, wherein four measurement classes are defined as a function of said exit state and said exit energy level, a first of said four measurement classes representing said exit state of unchanged phase and said exit energy level equal to said first energy level, a second of said four measurement classes representing said exit state of unchanged phase and said exit energy level equal to said second energy level, a third of said four measurement classes representing said exit state of finite phase shift and said exit energy level equal to said first energy level, and a fourth of said four measurement classes representing said exit state of finite phase shift and said exit energy level equal to said second energy level; and counting the number of said plurality of Rydberg atoms exiting said microwave field in each of said four measurement classes as an indication of the number of photons in said microwave field.

2. A method according to claim 1 wherein said step of generating said plurality of Rydberg atoms comprises the steps of:

generating a plurality of atoms having an energy level below that of said reference energy level;

exciting said plurality of atoms to an energy level equal to said reference energy level of said microwave field; and passing said plurality of atoms excited to said reference energy level through a microwave region having a frequency that is quasi resonant with a frequency corresponding to an energy difference between said first and second energy levels.

3. A method according to claim 2 wherein said plurality of atoms having an energy level below that of said reference energy level are monoenergetic.

4. A method according to claim 2 wherein said step of exciting utilizes laser and microwave energy transfer.

5. A method as in claim 2 wherein said microwave region is a Ramsey zone.

6. A method of counting photons in a single-mode, coherent microwave field having a known frequency associated therewith, comprising the steps of:

generating a plurality of atoms having an energy level below that of a reference energy level of said microwave field;

exciting said plurality of atoms to an energy level equal to said reference energy level of said microwave field;

passing said plurality of atoms excited to said reference energy level through an auxiliary microwave region wherein a plurality of Rydberg atoms are thereby generated, each of said plurality of Rydberg atoms having an energy state defined by a plurality of energy levels that includes a linear superposition of first and second energy levels and a third energy level, said first energy level being equal to said reference energy level of said microwave field, said second energy level being of different energy and opposite parity than that of said first energy level, and said third energy level having the same parity as that of said second energy level and being greater than said reference energy level such that a frequency associated with the difference between said third energy level and said first energy level is less than said known frequency of said microwave field by an amount $\delta$;

passing said plurality of Rydberg atoms through said microwave field one at a time;

measuring an exit state of said microwave field in terms of phase as each of said plurality of Rydberg atoms exits said microwave field, said exit state defining one of an unchanged phase in said microwave field or a finite phase shift in said microwave field;

detecting an exit energy level of each of said plurality of Rydberg atoms exiting said microwave field, said exit energy level being one of said first energy level and said second energy level, wherein first, second, third and fourth measurement classes are established as a function of said exit state and said exit energy level, said first measurement class representing said exit state of unchanged phase and said exit energy level equal to said first energy level, said second measurement class representing said exit state of unchanged phase and said exit energy level equal to said second energy level, said third measurement class representing said exit state of finite phase shift and said exit energy level equal to said first energy level, and said fourth measurement class representing said exit state of finite phase shift and said exit energy level equal to said second energy level; and counting the number of said plurality of Rydberg atoms exiting said microwave field in each of said first, second, third and fourth measurement classes to determine the number of photons N in said microwave field in accordance with the relationship $$N = \frac{l_n X}{\left(\cos\left[\left(\frac{v_0}{v}\right)\epsilon\right] - 1\right)}$$

wherein $$X = \frac{1}{4}\cot\left[\frac{\Omega'\tau}{2}\left(\frac{v_0}{v}\right)\right]\left[\left(\frac{1-a}{a}\right)^{1/2} + \left(\frac{1-b}{b}\right)^{-1/2}\right] + \frac{1}{4}\tan\left[\frac{\Omega'\tau}{2}\left(\frac{v_0}{v}\right)\right]\left[\left(\frac{1-c}{c}\right)^{1/2} + \left(\frac{1-d}{d}\right)^{-1/2}\right]$$

and $$\epsilon = \frac{\Omega_0^2}{2\delta}\left(\frac{L}{v_0}\right)$$

wherein $\Omega'$ is the Rabi coupling for said auxiliary microwave region, $\tau$ is the time it takes one of said plurality of atoms to travel through said auxiliary microwave region at reference speed $v_0$, $v_0/v$ is a ratio of reference speed-to actual speed of said one of said plurality of atoms traveling through said auxiliary microwave region, $\Omega_0$ is the Rabi coupling for said microwave field, L is the length of said microwave field traveled by each of said plurality of Rydberg atoms, and wherein $$a = \frac{J}{K+J},$$

$$b = \frac{K}{K+J},$$

$$c = \frac{P}{M+P},$$

$$d = \frac{M}{M+P},$$

where J is the count associated with said third measurement class, K is the count associated with said fourth measurement class, M is the count associated with said first measurement class, and P is the count associated with said second measurement class.

7. A method according to claim 6 wherein said plurality of atoms having an energy level below that of said reference energy level are monoenergetic.

8. Apparatus for determining numbers of photons in a single-mode, coherent microwave field, including:

storage cavity means for containing said single-mode, coherent microwave field;

means for injecting a plurality of Rydberg atoms into said storage cavity means one at a time;

means for non-destructively measuring an exit phase state of said microwave field as each of said plurality of Rydberg atoms exits said microwave field;

means for detecting an exit energy level of each of said plurality of Rydberg atoms exiting said microwave field; and means for counting said plurality of Rydberg atoms exiting said microwave field to determine the numbers of photons in said microwave field.

9. The apparatus as defined in claim 8 wherein each of said plurality of Rydberg atoms has an energy level defined as a linear superposition of first and second energy levels, said first energy level serving as a reference energy level of said microwave field and said second energy level being of different energy and parity than said first energy level, said exit energy level being one of said first and second energy levels, wherein four measurement classes are established as a function of said exit phase state and said exit energy level, a first of said four measurement classes representing the exit state of unchanged phase and said exit energy level equal to said first energy level, a second of said four measurement classes representing said exit state of unchanged phase and said exit energy level equal to said second energy level, a third of said four measurement classes representing said exit state of finite phase shift and said exit energy level equal to said first energy level, and a fourth of said four measurement classes representing said exit state of finite phase shift and said exit energy level equal to said second energy level.

10. The apparatus as defined in claim 9 wherein said means for injecting comprises:

generator means for providing said plurality of Rydberg atoms, comprising a source of atoms having an energy level below that of said reference energy level;

means for exciting said plurality of atoms from the source to an energy level equal to said reference energy level of said microwave field; and means for receiving said plurality of atoms excited to said energy level equal to said reference energy level within a microwave region from which said plurality of Rydberg atoms are outputted.

11. The apparatus as defined in claim 10 wherein said source produces monoenergetic atoms.

12. An apparatus as in claim 10 wherein said microwave region is a Ramsey zone.

* * * * *